United States Patent [19]

Joseph et al.

[11] 4,347,251

[45] Aug. 31, 1982

[54] NOVEL 3-SUBSTITUTED AMINO-1-SUBSTITUTED HETEROARYL-2-PYRAZOLINES

[75] Inventors: Joseph P. Joseph, Montvale, N.J.; John P. Dusza, Nanuet; Seymour Bernstein, New City, both of N.Y.

[73] Assignee: American Cyanamid Company, Stamford, Conn.

[21] Appl. No.: 282,827

[22] Filed: Jul. 13, 1981

[51] Int. Cl.$^3$ .................... A61K 31/44; C07D 401/04
[52] U.S. Cl. .................................. 424/263; 546/279
[58] Field of Search ...................... 546/279; 424/263

[56] References Cited

U.S. PATENT DOCUMENTS

| 3,169,966 | 2/1965 | Schmidt | 546/279 |
| 3,228,946 | 1/1966 | Schmidt | 546/279 |
| 3,228,947 | 1/1966 | Schmidt | 424/263 |

*Primary Examiner*—Jane T. Fan
*Attorney, Agent, or Firm*—Anne M. Rosenblum

[57] ABSTRACT

This disclosure describes novel 3-substituted amino-1-substituted heteroaryl-2-pyrazolines and their $C_4$ and $C_5$ analogs, effective as agents that ameliorate inflammation, analgesic agents, antibacterial agents and/or antifungal agents.

8 Claims, No Drawings

NOVEL 3-SUBSTITUTED AMINO-1-SUBSTITUTED HETEROARYL-2-PYRAZOLINES

PRIOR ART

1. R. Battisti, et. al., U.S. Pat. No. 4,149,005 (Apr. 10, 1979) discloses compounds of the formula:

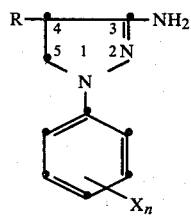

where R is H or $CH_3$, X is H, Br, Cl, alkyl, alkoxy or carboxyalkyl groups with from 1 to 4 carbon atoms or $CF_3$; and n is 1 or 2. These are disclosed as being used as intermediates in the preparation of 1-phenyl-3-aminopyrazoles as coupling components in azo dye manufacture. Related foreign patents: Ger. Offen. 2,727,706; French 2,355,834; Gr. Br. 1,515,500; Belgium 855,944; Netherland 7,706,760 and Japan 28,168.

2. G. A. Higgs, et. al., (Wellcome Research Laboratories); Biochemical Pharmacology, 28 1959 (1979) discloses 3-amino-1-[m-(trifluoromethyl)phenyl]-2-pyrazoline (BW 755C);

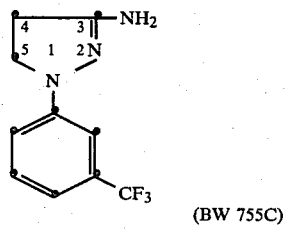

(BW 755C)

This compound is reported to have anti-inflammatory activity.

BRIEF SUMMARY OF THE INVENTION

This invention relates to new organic compounds and more particularly is concerned with novel 3-substituted amino-1-substituted heteroaryl-2-pyrazolines and their $C_4$ and $C_5$ analogs which may be represented by the following general formulae:

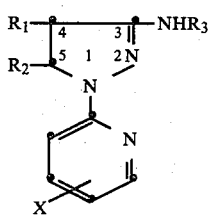

IV wherein $R_1$ and $R_2$ may be hydrogen and lower alkyl ($C_1$–$C_4$); $R_3$ is $-COCH_3$ and $-CHO$; X is halo and trifluoromethyl and the pharmacologically acceptable acid-addition salts thereof.

DETAILED DESCRIPTION OF THE INVENTION

The novel compounds of the present invention are generally obtainable as white to pale yellow crystalline solids having characteristic melting points and absorption spectra. The bases are appreciably soluble in solvents such as acetone, ethanol, toluene, methylene chloride and the like but are relatively insoluble in water. The organic bases of the present invention form non-toxic acid-addition salts with a variety of pharmacologically acceptable organic and inorganic salt forming reagents. Thus, acid-addition salts, formed by admixture of the organic free base with one or two equivalents of an acid, suitably in a neutral solvent, are formed with such acids as sulfuric, phosphoric, hydrochloric, hydriodic, sulfamic, citric, lactic, fumacic, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

Preparation of the novel 3-substituted amino-1-substituted heteroaryl-2-pyrazolines IV of the instant invention, which are either anti-inflammatory agents, analgesic agents, antibacterial and/or antifungal agents is accomplished by the adaptation of the procedure of Duffin, G. F. and Kendall, J. D., J. Chem. Soc. 1954, 408; in accordance with the following reaction scheme:

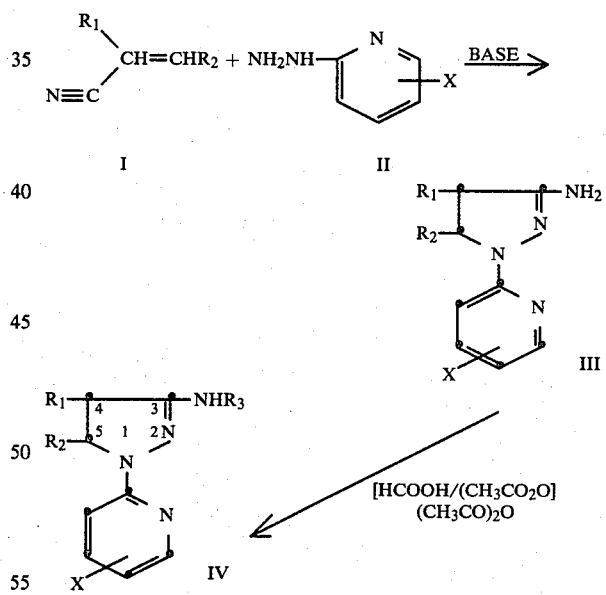

wherein $R_1$, $R_2$ and $R_3$ and X are as hereinabove defined.

In accordance with the above reaction scheme an X substituted hereroarylhydrazine II such as 2-chloro-6-hydrazinopyridine, 3-chloro-6-hydrazinopyridine, 6-hydrazino-2-trifluoromethylpyridine or 5-chloro-2-hydrazinopyridine and the like is reacted with a $\alpha,\beta$-unsaturated nitrile I, such as acrylonitrile, methacrylonitrile, crotononitrile, cinnamonitrile, 3-methoxyvaleronitrile, or compounds such as $\beta$-ethoxypropionitrile (which can undergo base catalyzed elimination to yield I) in a base such as sodium ethoxide or choline hydrate in absolute ethanol. The reaction mixture is refluxed for a period of from 2-18 hours then the solvent is removed in vacuo. The addition of water gives a filterable solid which is collected, dissolved in dichloromethane and passed through a short column of a hydrous magnesium silicate. The column effluent is then refluxed on a steam bath with the gradual addition of hexane until crystallization is noted. Recrystallization from the same solvent pair with or without additional treatment with a hydrous magnesium silicate) or from acetone-hexane provides the 3-amino-2-substituted heteroaryl-2-pyrazoline compounds III. If the pyrazoline III is not soluble in dichloromethane, recrystallization may be accomplished from acetone-hexane, 95% ethanol or benzene with the omission of the hydrous magnesium silicate treatment phase.

The pyrazoline compound III is subjected to N-acylation by treating with an acylating agent such as a mixture of formic acid and acetic anhydride (Feiser and Feiser, Reagents for Organic Synthesis, Vol. 1, page 4), or acetic anhydride (with or without a catalyst such as 4-dimethylaminopyridine) at room temperature for 2-48 hours to yield the corresponding novel 3-substituted amino-1-substituted heteroaryl-2-pyrazoline derivatives IV of the present invention which for the most part may be recrystallized from dichloromethane-hexane or acetone-hexane.

The compounds of the instant invention have utility as pharmacological agents. They are active either as anti-inflammatory agents, analgesic agent, antibacterial and/or antifungal agents and in some cases are active in more than one of these areas.

Representative compounds of the present invention have proven to be active in vivo as anti-inflammatory agents when tested by the Carageenin Induced Edema of the Rat Paw Test. This test is a modification of the method of Winter, C.A., et al., Proc. Soc. Exp. Biol. and Med., 111, 544 (1962). Compounds found to be active in this test are:

N-[1-(6-Chloro-2-pyridyl)-2-pyrazolin-3-yl]acetamide
N-[1-(6-Chloro-2-pyridyl)-2-pyrazolin-3-yl]formamide.

The compounds of the present invention also possess activity as analgesic agents. A method employed for measuring the in vivo activity of the compounds of the present invention is the "writhing syndrome" test for analgesic activity as described by Siegmund, et al., Proceedings of the Society for Experimental Biology and Medicine, 95, 729 (1957), with modifications as described in U.S. Pat. No. 3,863,010. A representative compound of the present invention which is active when tested by the "writhing syndrome" test is:

N-[1-(6-Chloro-2-pyridyl)-2-pyrazolin-3-yl]acetamide

Representative compounds of the present invention have been proven active in vitro as antibacterial and/or anti-fungal agents when tested by such procedures as the standard agar dilution procedure. Compounds proven active in this test include:

N-[1-(6-Chloro-2-pyridyl)-4-methyl-2-pyrazolin-3-yl]acetamide
N-[1-(6-Chloro-2-pyridyl)-5-ethyl-2-pyrazolin-3-yl]acetamide
N-[1-(6-Chloro-2-pyridyl)-2-pyrazolin-3-yl]formamide The compounds of the present invention have been found to be highly useful for meliorating inflammation as analgesic agents, antibacterial and antifulgal agents in mammals, when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, intra-articular, topical or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for the purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The compounds of this invention are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin, excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives a dye and flavoring such as cherry or orange flavor. Of course, any material used in preparing any dosage unit form should be pharmaceutically pure and substantially non-toxic in the amounts employed.

This invention will be described in greater detail in conjunction with the following examples:

EXAMPLE I

N-[1-(6-Chloro-2-pyridyl)-4-methyl-2-pyrazolin-3-yl]acetamide

A mixture of 100 g. of 2,6-dichloropyridine in 2-ml. of hydrazine hydrate is stirred and refluxed for 5 hours. The reaction mixture is cooled and filtered. The product is washed with water and dried to give 47.7 g. of 2-chloro-6-hydrazinopyridine, m.p. 117°–119° C.

A 500 mg. amount of sodium metal is dissolved in 100 ml. of absolute ethanol, then 15.0 g. of 2-chloro-6-hydrazinopyridine is added followed by 7.2. g. of methacrylonitrile. The reaction mixture is refluxed for 18 hours. The solvent is removed in vacuo and water is added to the residue to separate a solid. The solid is collected by filtration, dissolved in dichloromethane, dried over magnesium sulfate, and filtered through a hydrous magnesium silicate. The effluent is concentrated while adding hexane to crystallize 15.0 g. of 2-(3-amino-4-methyl-2-pyrazolin-1-yl)-6-chloropyridine as a tan solid, m.p. 170°–175° C.

A mixture of 10.0 g. of the preceding compound, 500 mg. of 4-dimethylaminopyridine and 50.0 ml. of acetic anhydride is stirred for 10 minutes at room temperature to achieve solution. The solution is allowed to stand at room temperature for 18 hours to separate a solid. The whole mixture is poured into water and after standing one hour the solid is collected by filtration. The solid is dissolved in dichloromethane. This solution is washed with water then dried over magnesium sulfate and evaporated in vacuo to give a solid. The solid is dissolved in 100 ml. of methanol and 10.0 ml. of 1 N potassium hydroxide in methanol is added. After one hour at room temperature the organic solvent is removed in vacuo and water is added to separate a solid. The solid is collected, washed with water and dried to give 8.7 g. of product. A 500 mg. amount is recrystallized from dichloromethane-hexane to give 408 mg. of the product of the Example as pink crystals, m.p. 166°–167° C.

EXAMPLE 2

N-[1-(6-Chloro-2-pyridyl)-5-ethyl-2-pyrazolin-3-yl]acetamide

A solution of 124 g. of sodium methylate in 414 g. of methanol, diluted with 51 ml. of N,N-dimethylformamide is added via a dropping funnel to a stirred solution of 100 g. of diethylcyanomethylphosphorate and 35 g. of freshly distilled propionaldehyde in 75. ml of N,N-dimethylformamide maintained at 40°–45° C. in an ice bath. After the addition is completed the reaction mixture is warmed to 50° C. and stirring is continued for one hour without further external heating or cooling. The reaction mixture is diluted with 270 ml. of 50:50 methanol-water then the pH of the mixture is adjusted to pH 7.0 with glacial acetic acid and the neutral solution is extracted thoroughly with ether. The combined ether extracts are washed with dilute acetic acid then, with water. The organic layer is dried over magnesium sulfate, filtered and concentrated in vacuo to an oil. The oil is distilled through a 2 foot saddle filled column, giving 29.0 g. of 3-methoxyvaleronitrile, b.p. 42° C. at 3 mm., $n_D^{25°}$ 1.4190.

A 500 mg. amount of sodium metal is dissolved in 100 ml. of absolute ethanol, then 15.0 g. of 2-chloro-6-hydrazinopyridine (Example 1) is added followed by 11.0 g. of 3-methoxyvaleronitrile. The reaction mixture is refluxed for 18 hours, then is evaporated in vacuo to give a solid. The solid is dissolved in water/dichloromethane. The organic layer is separated, dried over magnesium sulfate, filtered through hydrous magnesium silicate and concentrated while adding hexane to yield 14.3 g. of 2-(3-amino-5-ethyl-2-pyrazolin-1-yl)-6-chloropyridine as light yellow crystals, m.p. 125°–127° C.

A mixture of 9.3 g. of the preceding compound, 500 mg. of 4-dimethylaminopyridine and 50.0 ml. of acetic anhydride is stirred until the solid gradually dissolves. The solution is allowed to remain at room temperature for 18 hours. The solution is then added to water to separate a solid. After standing for one hour the solid is collected by filtration and dissolved in 50 ml. of methanol, then 10 ml. of 1 N potassium hydroxide in methanol is added. After standing at room temperature for 30 minutes this mixture is added to water to separate a solid. The solid is collected and dried to give 6.9 g. of crude product. A 300 mg. amount of this material is recrystallized from dichloromethane-hexane to yield 252 mg. of the desired product as white crystals, m.p. 170°–171° C.

EXAMPLE 3

N-[1-(6-Chloro-2-pyridyl)-2-pyrazolin-3-yl]acetamide

A 0.32 g. amount of sodium metal is dissolved in 100 ml. of absolute ethanol, then 10.0 g. of 2-chloro-6-hydrazinopyridine (Example 1) is added, followed by 4.0 g. of acrylonitrile. The reaction mixture is refluxed for 18 hours. The solvent is removed in vacuo and water is added to the residue to separate a solid. The solid is collected by filtration, dissolved in dichloromethane, dried over magnesium sulfate, filtered through magnesium silicate and concentrated while adding hexane, to separate crystals. The mixture is cooled and filtered to give 9.3 g. of 2-(3-amino-2-pyrazolin-1-yl)-6-chloropyridine as a pale yellow solid, m.p. 143°–145° C.

A mixture of 5.0 g. of the above compound, 50 mg. of 4-dimethylamino pyridine and 25.0 ml. of acetic anhydride is allowed to stand at room temperature for 16 hours. The solid formed is collected by filtration, washed with cold acetic anhydride then with hexane to give 2.25 g. of crude product. This material is dissolved in acetone. The solution is passed through a hydrous magnesium silicate and the filtrate is concentrated while adding hexane to crystallize 1.62 g. of the desired product as colorless needles, m.p. 209°–211.5° C.

EXAMPLE 4

N-[1-(6-Chloro-2-pyridyl)-2-pyrazolin-3-yl]formamide

A mixture of 5.0 g. of 2-(3-amino-2-pyrazolin-1-yl)-6-chloropyridine (prepared as described in Example 3) and 25 ml. of a mixture of formic acid and acetic anhydride (Feiser and Feiser, Reagents for Organic Synthesis, Vol. 1, page 4) at room temperature gives an immediate yellow precipitate. The precipitate is collected by filtration then is recrystallized from acetone-hexane to give 3.05 g. of the product of the Example as off-white crystals, m.p. 190°–192° C.

EXAMPLE 5

Preparation of Compressed Tablet

| Ingredient | mg./tablet |
| --- | --- |
| Active Compound | 0.5–500 |
| Dibasic Calcium Phosphate N.F. | qs |
| Starch USP | 40 |
| Modified Starch | 10 |
| Magnesium Stearate USP | 0.1–5.0 (% w/w) |

EXAMPLE 6

Preparation of Compressed Tablet

| Ingredient | mg./tablet |
| --- | --- |
| Active Compound | 0.5–500 |
| Dibasic Calcium Phosphate N.F. | qs |
| Starch USP | 40 |
| Modified Starch | 10 |
| *Surfactant, e.g. Sodium Lauryl Sulfate | 0.1–2.0 (% w/w) |
| Magnesium Stearate USP | 0.1–5.0 (% w/w) |

*Other surface active agents such as disodium sulfosuccinate and nonionic surface active agents such as Spano ® and Tween ® may also be employed.

EXAMPLE 7

Preparation of Compressed Tablet

| Ingredient | mg./tablet |
| --- | --- |
| Active Compound | 0.5–500 |
| Direct Compression Sugar Agent e.g. Emdex | qs |
| Magnesium Stearate | 0.1–3.0 (% w/w) |

EXAMPLE 8

Preparation of Hard Shell Capsule

| Ingredient | mg./capsule |
| --- | --- |
| Active Compound | 0.5–500 |
| Lactose, Spray Dried | qs |
| Magnesium Stearate | 0.1–3.0 (% w/w) |

EXAMPLE 9

Preparation of Oral Liquid (Syrup)

| Ingredient | % w/v |
| --- | --- |
| Active Compound | 0.05–5 |
| Liquid Sugar | 75.0 |
| Methyl Paraben USP | 0.18 |
| Propyl Paraben USP | 0.02 |
| Suspending Agent e.g. Avicel | 0.5–1.0 |
| Flavoring Agent | qs |
| Purified Water qs ad | 100.0 |

EXAMPLE 10

Preparation of Oral Liquid (Elixir)

| Ingredient | % w/v |
| --- | --- |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 11

Preparation of Oral Suspension (Syrup)

| Ingredient | % w/v |
| --- | --- |
| Active Compound | 0.05–5 |
| Polysorbate 80 USP | 0.1 |
| Magnesium Aluminum Silicate, Colloidal | 0.3 |
| Dye | 0.001–0.5 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 12

Preparation of Injectable Solution

| Ingredient | % w/v |
| --- | --- |
| Active Compound | 0.05–5 |
| Benzyl Alcohol N.F. | 0.9 |
| Water for Injection | 100.0 |

EXAMPLE 13

Preparation of Injectable Oil

| Ingredient | % w/v |
| --- | --- |
| Active Compound | 0.05–5 |

-continued

| Ingredient | % w/v |
| --- | --- |
| Benzyl Alcohol | 1.5 |
| Sesame Oil qs ad | 100.0 |

EXAMPLE 14

Preparation of Intra-articular Product

| Ingredient | Amount |
| --- | --- |
| Active Compound | 2–20 mg. |
| NaCl (physiological saline) | 0.9% |
| Benzyl Alcohol | 0.9% |
| Sodium Carboxymethylcellulose pH adjusted to 5.0–7.5 | 1–5% |
| Water for Injection qs ad | 100% |

EXAMPLE 15

Preparation of Injectable Depo Suspension

| Ingredient | % w/v |
| --- | --- |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 16

Preparation of Topical Cream

| Ingredient | % w/v |
| --- | --- |
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 17

Preparation of Topical Ointment

| Ingredient | % w/v |
| --- | --- |
| Active Compound | 0.05–5 |
| Cholesterol | 3 |
| Stearyl Alcohol | 3 |
| White Wax | 8 |
| Petrolatum, White USP qs | 100 |

We claim:

1. A compound selected from the group consisting of those of the formula:

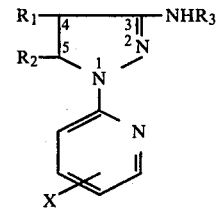

wherein $R_1$ and $R_2$ may be hydrogen or lower alkyl ($C_1$–$C_4$); $R_3$ is -COCH$_3$ or -CHO; X is halo or trifluoromethyl or a pharmacologically acceptable acid-addition salt thereof.

2. The compound according to claim 1, N-[1-(6-chloro-2-pyridyl)-4-methyl-2-pyrazolin-3-yl]acetamide.

3. The compound according to claim 1, N-[1-(6-chloro-2-pyridyl)-5-ethyl-2-pyrazolin-3-yl]acetamide.

4. The compound according to claim 1, N-[1-(6-chloro-2-pyridyl)-2-pyrazolin-3-yl]acetamide.

5. The compound according to claim 1, N-[1-(6-chloro-2-pyridyl)-2-pyrazolin-3-yl]formamide.

6. The method of meliorating inflammation in a mammal which comprises administering to said mammal an effective anti inflammatory amount of a compound according to claims 1, 2, 3, 4 or 5.

7. The method of treating pain in a mammal which comprises administering to said mammal an effective analgetic amount of a compound according to claim 1, 2, 3 or 4.

8. The method of treating bacterial and/or fungal infections in a mammal which comprises administering to said mammal an effective antibacterial and/or antifungal amount of a compound according to claims 1, 2, 3 or 4.

* * * * *